US011412937B2

(12) United States Patent
Ahmad et al.

(10) Patent No.: US 11,412,937 B2
(45) Date of Patent: Aug. 16, 2022

(54) MULTI-PERSON VITAL SIGNS MONITORING USING MILLIMETER WAVE (MM-WAVE) SIGNALS

(71) Applicant: Texas Instruments Incorporated, Dallas, TX (US)

(72) Inventors: Adeel Ahmad, Richardson, TX (US); Dan Wang, Allen, TX (US); June Chul Roh, Allen, TX (US)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 750 days.

(21) Appl. No.: 15/717,756

(22) Filed: Sep. 27, 2017

(65) Prior Publication Data

US 2018/0279884 A1  Oct. 4, 2018

Related U.S. Application Data

(60) Provisional application No. 62/478,297, filed on Mar. 29, 2017.

(51) Int. Cl.
*A61B 5/00* (2006.01)
*A61B 5/0205* (2006.01)
*A61B 5/08* (2006.01)
*A61B 5/024* (2006.01)
*A61B 5/0507* (2021.01)

(52) U.S. Cl.
CPC ............ *A61B 5/0205* (2013.01); *A61B 5/725* (2013.01); *A61B 5/7214* (2013.01);
(Continued)

(58) Field of Classification Search
CPC ... A61B 5/0205; A61B 5/7214; A61B 5/7278; A61B 5/7257; A61B 5/725;
(Continued)

(56) References Cited

U.S. PATENT DOCUMENTS 5,859,609 A * 1/1999 Sheen ................. G01S 7/412
342/179
2008/0077015 A1* 3/2008 Boric-Lubecke .... A61B 5/0507
600/453
(Continued)

OTHER PUBLICATIONS

Z. Yang, P. Pathak, Y. Zeng, X. Liran, and P. Mohapatra, "Monitoring vital signs using millimeter wave," in Proc. IEEE MobiHoc'16, Paderborn, Germany, Jul. 2016.*
(Continued)

*Primary Examiner* — Jonathan Cwern
*Assistant Examiner* — Amal Aly Farag
(74) *Attorney, Agent, or Firm* — Carl G. Peterson; Charles A. Brill; Frank D. Cimino

(57) ABSTRACT

A mm-wave system includes transmission of a millimeter wave (mm-wave) signal by a plurality of transmitters to multiple objects, and receiving of return-mm-wave signals from the multiple objects by a plurality of receivers. A processor is configured to perform an algorithm to derive complex-valued samples and angle measurements from each receiver to identify one object from another object. The processor further extracts signal waveforms that correspond to each object and process the extracted signal waveforms to estimate breathing rate and heart rate of the identified object.

20 Claims, 9 Drawing Sheets

(52) U.S. Cl.
CPC .......... *A61B 5/7257* (2013.01); *A61B 5/7278* (2013.01); *A61B 5/02444* (2013.01); *A61B 5/0507* (2013.01); *A61B 5/0816* (2013.01)

(58) Field of Classification Search
CPC . A61B 5/0507; A61B 5/02444; A61B 5/0816; A61B 5/1135
See application file for complete search history.

(56) References Cited

U.S. PATENT DOCUMENTS

| | | | | |
|---|---|---|---|---|
| 2010/0130873 | A1* | 5/2010 | Yuen | A61B 5/721 |
| | | | | 600/484 |
| 2010/0316158 | A1* | 12/2010 | Arne | H04B 1/1027 |
| | | | | 375/285 |
| 2015/0253419 | A1* | 9/2015 | Alland | G01S 13/4463 |
| | | | | 342/385 |
| 2018/0166794 | A1* | 6/2018 | Raphaeli | H01Q 21/28 |

OTHER PUBLICATIONS

Wang, G., et al. "Application of Linear-Frequency-Modulated Continuous-Wave (LFMCW) Radars for Tracking of Vital Signs," Microwave Theory and Techniques, IEEE Transactions on 62(6): 1387-1399, Jun. 2014, 13 pages.

Adib, F., et al. Smart Homes that Monitor Breathing and Heart Rate. Proceedings of the 33rd Annual ACM Conference on Human Factors in Computing Systems, Seoul, Republic of Korea, ACM: 837-846, 2015, 10 pages.

* cited by examiner

MULTI-PERSON VITAL SIGNS MONITORING USING MILLIMETER WAVE (MM-WAVE) SIGNALS

RELATED APPLICATIONS

This application claims the benefit of priority of U.S. Provisional Patent Application Ser. No. 62/478,297 filed Mar. 29, 2017, incorporated herein by reference.

BACKGROUND

Radar systems have been used by commercial, private, and military sectors to detect presence and track locations of relatively large, fast moving targets. For example, the radar systems have been used to track targets such as rockets, people, automobiles, aircraft, etc. In another example, the radar systems have been used indoors to detect objects in manufacturing assembly, etc.

Presently, radar systems are being explored for use in numerous medical and diagnostic applications ranging from cancer imaging to glucose monitoring. For example, vital signs (breathing-rate and heart-rate) measurements methods may require body-contact of monitoring devices such as wearing chest-bands (for heart-rate monitoring) or attaching a nasal probe (for breathing-rate). In recent years, camera or radar-based non-contact methods have also been proposed; however, these have their own limitations such as camera-based methods that may require optimum lighting conditions during operation. Furthermore, the radar-based non-contact methods that use a continuous wave (CW) Doppler radar is prone to interference from noise and other moving/vibrating sources (such as another person) within radar field-of-view.

SUMMARY

Described herein is a technology for a vital signs monitoring of multiple objects using a mm-wave system. Particularly, the mm-wave system includes a plurality of transmitters configured to transmit mm-wave signals to the multiple objects. In return, a plurality of receivers of the mm-wave system receives return-mm-wave signals from the multiple objects. The mm-wave system further includes a processor configured to perform a Fast Fourier Transform (FFT) algorithm to derive complex-valued samples and angle measurements from each receiver of the plurality of receivers to identify one object from another object. For each identified object, the processor may extract signal waveforms that correspond to the identified object and process the extracted signal waveforms to estimate breathing rate and heart rate of the identified object.

BRIEF DESCRIPTION OF THE DRAWINGS

The detailed description is described with reference to accompanying figures. In the figures, the left-most digit(s) of a reference number identifies the figure in which the reference number first appears. The same numbers are used throughout the drawings to reference like features and components.

DETAILED DESCRIPTION

Figure 1:
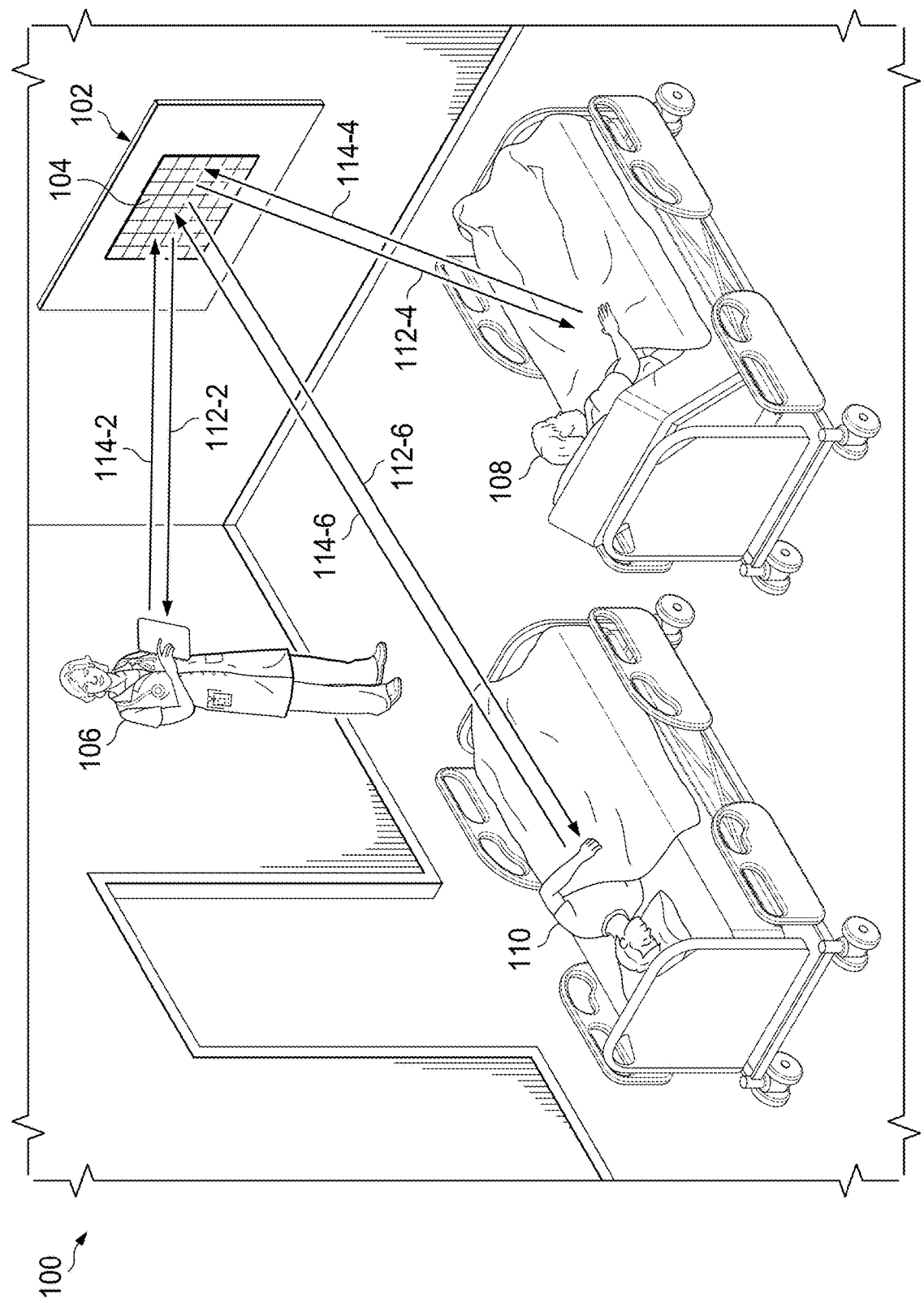
FIG. 1 illustrates an example scenario illustrating an example application of a millimeter-wave (mm-wave) system as described herein.

FIG. 1 is an example scenario 100 illustrating an example application of a mm-wave system as described herein. The mm-wave system, for example, may detect and identify each object from multiple objects (e.g., multiple persons). Thereafter, the mm-wave system may estimate breathing and heart rates of each identified person.

As shown, the scenario 100 includes, for example, a device 102 with a mm-wave system (i.e., a system-on-a-chip) 104, a nurse that is represented by a first object 106, a patient represented as a second object 108, another patient represented as a third object 110, transmitted mm-wave signals 112, and reflected return-mm-wave signals 114.

The device 102, for example, may be a wireless medical monitoring machine that is used in a hospital recovery room, neo-natal intensive care unit (NICU) room to monitor young babies, ICU, or a clinic. The device 102 may also be a safety monitoring device that is integrated to a dashboard of a car in order to detect vital signs of a driver or a passenger. Furthermore, the device 102 may be used in an animal clinic where non-contact vital signs measurement, for example, of a dog is performed by veterinarians.

As opposed to digital cameras that may be used for non-contact vital signs measurements, the mm-wave system 104 may be configured, for example, to transmit W band mm-wave signals to detect and determine locations of the first object 106, second object 108, and/or third object 110 even on a zero-visibility environment, or in case where the objects are blocked by a curtain, blanket or other structure. In this example, the mm-wave system 104 may be a system-on-chip (SOC) that operates at the mm wave band mm-wave signals to the direction of the objects.

The mm-wave system 104 transmits, for example, the W band-mm-wave signals 112-2 to the direction of the first object 106. In response to this transmission, the mm-wave system 104 may receive return-mm-wave signals 114-2 from the first object 106 using the same transmission channel. Similarly, the mm-wave system 104 may transmit the mm-wave signals 112-4 and 112-6 to the directions of the second object 108 and third object 110, respectively. In response to these transmissions, the mm-wave system 104 may receive return-mm-wave signals 114-4 and 114-6 from the second object 108 and third object 110, respectively.

In the examples above, the mm-wave system 104 may be configured to use the received return-mm-wave signals 114-2 to 114-6 in order to detect presence of the first object 106, second object 108, and the third object 110, respectively. As further discussed below, the mm-wave system 104 may utilize, for example, frequency-modulated continuous wave (FMCW) mm-wave signals and multiple transmit and receive channels in order to separate multiple targets/objects from one another.

Although the example basic block diagram of the device 102 illustrates in a limited manner the basic components, other components such as processors, storage, applications, memory, etc. are not described in order to simplify the embodiments described herein.

Figure 2:
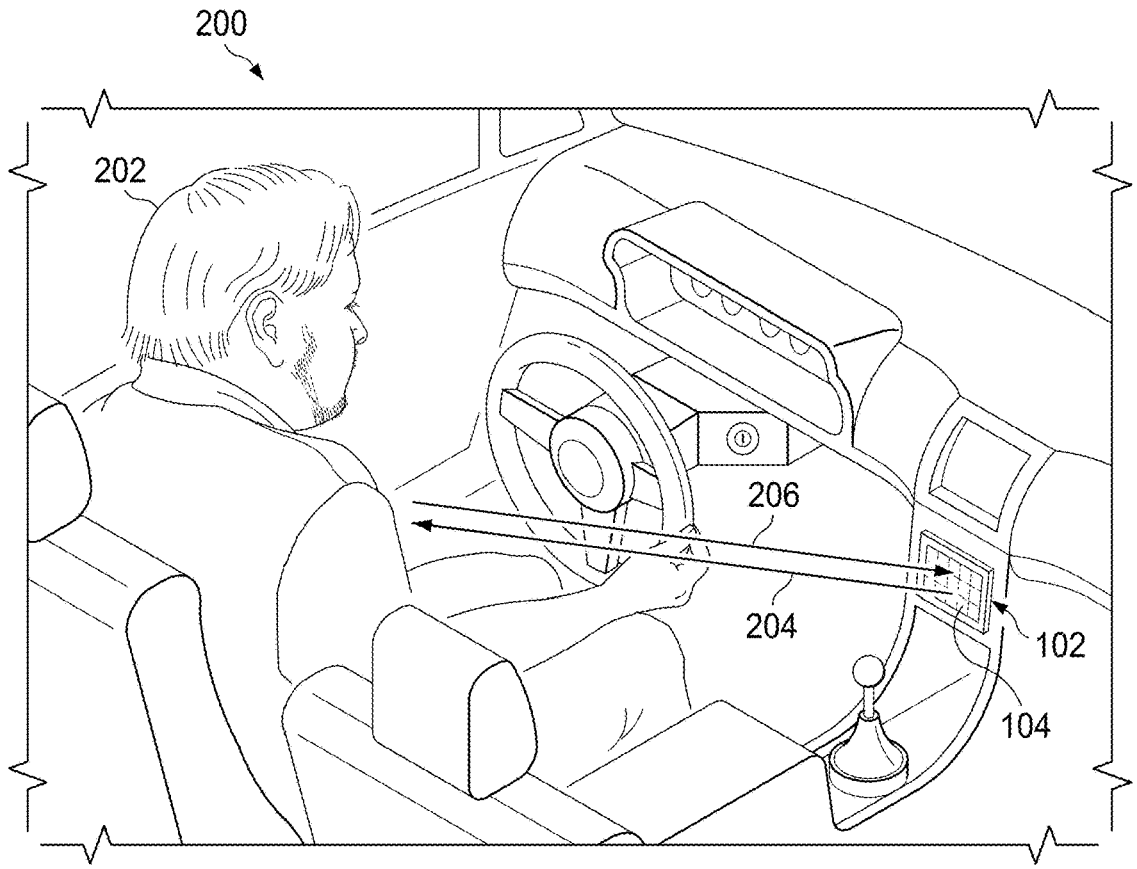
FIG. 2 illustrates another example scenario illustrating an example application of a millimeter-wave (mm-wave) system as described herein.

FIG. 2 is an example scenario 200 illustrating another example application of a mm-wave system as described herein. As shown, the device 102 is disposed on a dashboard of a car in order to detect vital signs information of a driver 202. The vital signs information, for example, may indicate that the driver is drowsy and the device 102 may be configured to alert the driver 202 to take a brief rest, take medication, or the other action.

Similar to FIG. 1 above, the mm-wave system 104 may transmit mm-wave signal 204 and receive return-mm-wave signals 206 in order to estimate breathing and heart rates of the driver 202. For example, the received return-mm-wave signals 206 may be processed to isolate breathing signal waveforms from heart rate-signal waveforms and measure the instantaneous heart-rates. In this example, the device 102 may be pre-configured to measure the changes in the instantaneous heart-rates and give an alert once the estimated breathing-rate or changes in the instantaneous heart-rate is above/below a certain threshold. The changes in the instantaneous heart-rates might be indicative, for example, of driver 202 fatigue or drowsiness.

Figure 3:
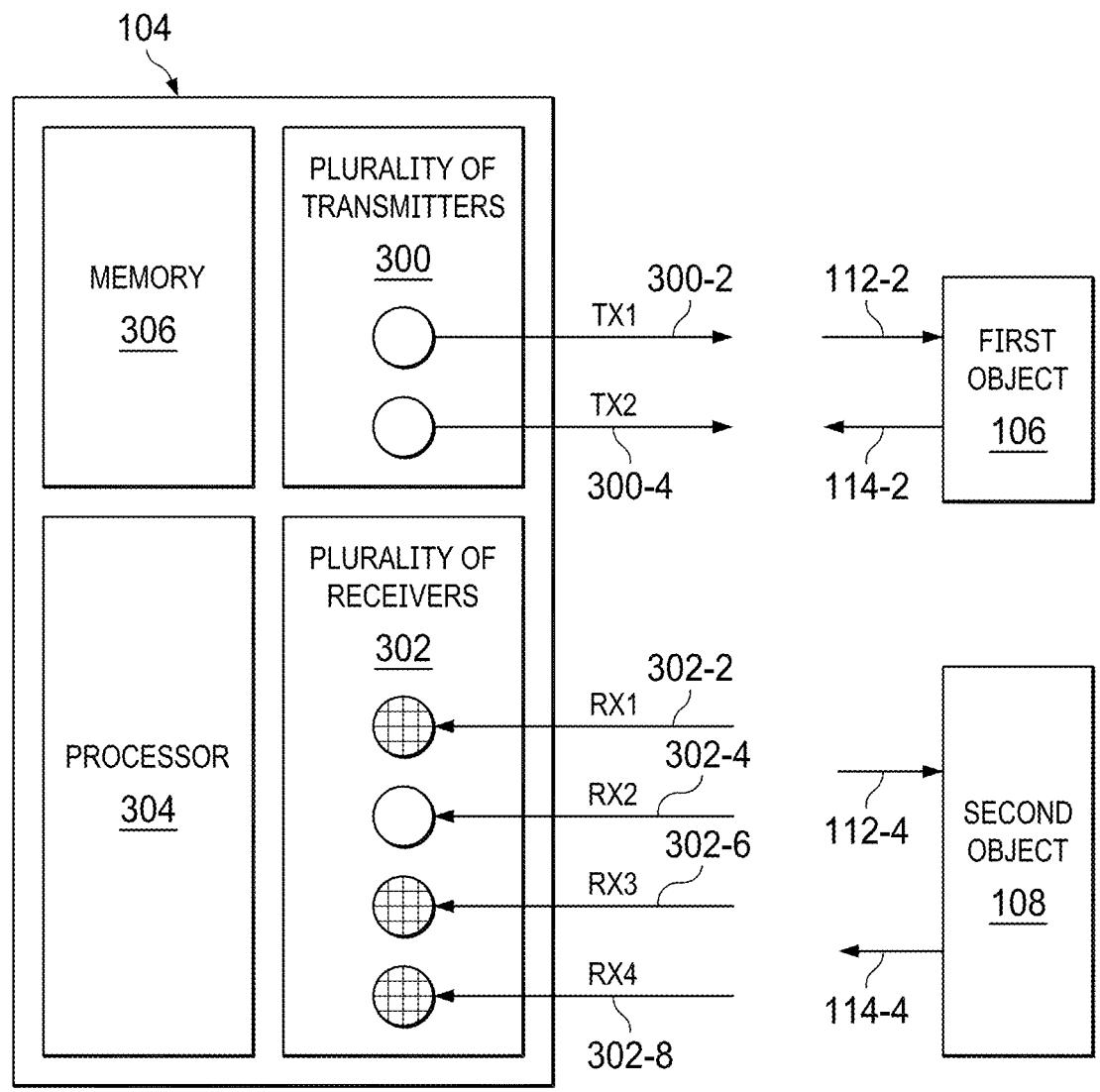
FIG. 3 illustrates an example mm-wave system as described in present implementations herein.

FIG. 3 illustrates an example mm-wave system 104 as described in present implementations herein. As shown, the example mm-wave system 104 may include a plurality of transmitters or transmitter channels 300, a plurality of receivers or receiver channels 302, a processor 304, and a memory 306. The plurality of transmitters 300 and the plurality of receivers 302 may be cascaded, for example, to generate large number of virtual antennas. The use of large number of virtual antennas may allow the estimation of angles to identify and isolate the multiple objects from one another that are at the same radial distance from the device 104. In this example, combining the two transmitters (i.e., TX1 300-2 and TX2 300-4) with the four receivers (i.e., RX1 302-2, RX2 302-4, RX3 302-6, and RX4 302-8) of the plurality of receivers 302 may generate eight virtual antennas for a multi-input multi-output (MIMO) antenna system.

For example, the mm-wave signal 112 may be transmitted through the plurality of transmitters 300 in a time division multiplexing format. That is, the mm-wave signal 112 is first transmitted through TX1 300-2 and received by each receiver of the plurality of receivers 302. Thereafter, mm-wave signal 112 is re-transmitted through TX2 300-4 and received by each receiver of the plurality of receivers 302. In this example, TX1 300-2 and TX2 300-4 are placed 2X apart from one another and the spacing between RX1 302-2 and RX1 302-4, RX1 302-4 and RX1 302-6, RX1 302-6 and RX1 302-8 is $\lambda/2$ where $\lambda$ is the wavelength, hence a virtual linear array of 8 receivers may be formed. In this example still, the mm-wave signal 112 may be transmitted to the first object 106 and the second object 108. Although the plurality of transmitters 300 in FIG. 3 shows a couple of different transmitters in transmitting the mm-wave signals, additional number of transmitters may be added and utilized without affecting the implementations described herein.

In an implementation, the processor 304 may be configured to process the received return-mm-wave signals 114-2 and 114-4. For example, the processor 304 may be configured to identify and isolate each object or target by identifying range and angle of each object based on the received return-mm-wave signals 114-2 and 114-4. The detection and identification of the range and angle, and the estimation of vital signs measurements of the identified objects are further discussed below.

The memory 306, for example, may be coupled to the processor 304 via a bus and is further operable to instructions or commands that are executable by the processor 304. For example, the instruction or commands include performing one or more functions such as the performing of the FFT algorithm.

Figure 4:
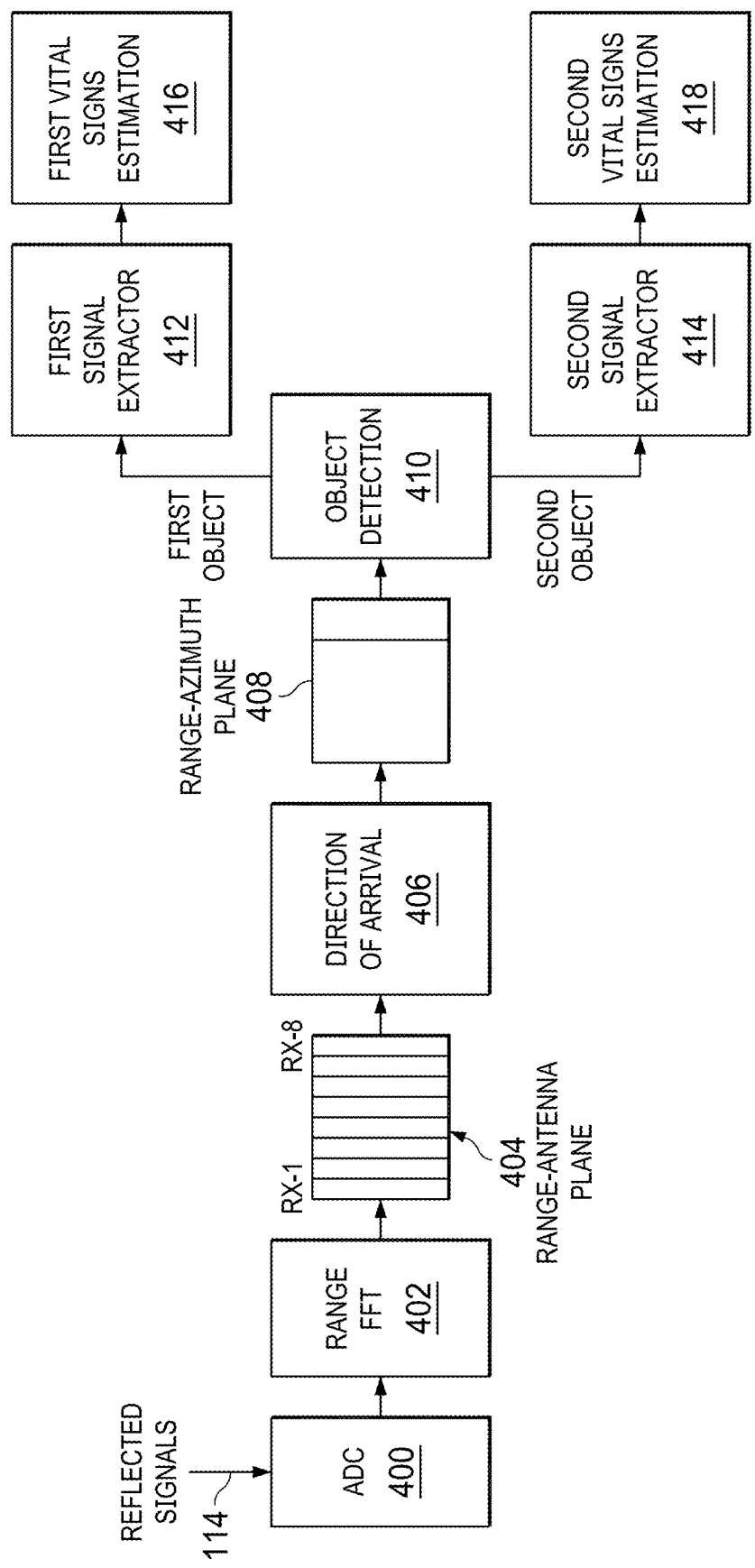
FIG. 4 illustrates an example detection and identification of multiple objects by a mm-wave system as described in present implementations herein.

FIG. 4 illustrates an example detection and identification of multiple objects by a mm-wave system as described in present implementations herein. Particularly, the detection and identification may relate to multiple persons (e.g., first object 106, second object 108, etc.) whose vital signs are measured through the mm-wave system as described herein.

Referencing FIG. 4, an analog to digital converter (ADC) 400 may receive and convert the analog reflected mm-wave signals 114 (i.e., signal reflections from multiple persons) into digital reflected mm-wave signals 114. In certain implementations, an ADC front end 400 may receive the signals 114 and convert the signals 114 to a digitized stream of data. The digitized stream of data is a combination of all the reflected signals 114-2, 114-4, 114-6 from different objects within the scene. A range-FFT 402 receives and further processes in time-domain the digitized stream of data. For example, the range-FFT 402 may be configured to perform an FFT algorithm in order to transform the time-domain digitized stream of data into frequency-domain digital digitized stream of data where the different frequency components of the signal corresponds to the ranges (radial distances) of the objects from the device 104. In this example, an output of the range-FFT 402 may include complex-valued samples (i.e., samples with magnitudes and phases) for each receiver of the plurality of receivers 302. The different signal magnitudes and signal phases on each receiver of the plurality of receivers 302 may be utilized to identify and distinguish one reflecting object from another reflecting object.

For example, the output of the range-FFT 402 for each receiver i.e., the complex-valued samples of each receiver of the plurality of receivers 302, are concatenated to generate a range-antenna plane 404. In a 2TX by 4RX mm-wave system that may generate a total of eight virtual receivers, the range-antenna plane 404 may include a series of combined complex-valued samples from each of the 8 virtual receivers. The series of combined complex-valued samples may include the signal magnitudes and phases as seen from the eight virtual receivers (i.e., plurality of receivers 302).

Based from the concatenated complex-valued samples from the range-antenna plane 404, a direction of arrival 406 may be configured to perform a determination of an angle of arrival of the reflecting objects. For example, the direction of arrival 406 may perform beamforming or another FFT algorithm along the RX-dimension for each range-bin from the range-antenna plane 404. The direction of arrival may be performed individually on each of the range-bins or may be performed on the range-bins corresponding to the detected objects after applying a suitable detection algorithm like CFAR (Constant False Alarm Rate). In this example still, an output of the direction of arrival 406 may be represented by a derived or formed range-azimuth plane 408.

The range-azimuth plane 408, for example, may include corresponding azimuth or angle measurements for the concatenated complex-valued samples. In this example, although the multiple objects may have the same range, the azimuth angle measurements may facilitate identification of the multiple objects based on the differences of angle measurements. In this case, an object detection 410 may be configured to determine the different objects based from the range-azimuth plane 408 by utilizing, for example, a constant false alarm rate (CFAR) algorithm or other types of detection schemes to determine the different objects.

After the determination and identification of the different objects, each object such as the first object 106 and the second object 108 may be processed by an example first signal extractor 412 and a second signal extractor 414, respectively. For example, the first signal extractor 412 and the second signal extractor 414 may be configured to extract the phase value in the range-azimuth plane 408 based on the range-angle bin identified for each of the multiple objects. These phase values are tracked over time by a user-determined window length which can be from 5-30 seconds. In this example, the first signal extractor 412 and the second signal extractor 414 may extract the signals that correspond to the first object 106 and the second object 108, respectively.

In an implementation, and for the first object 106 above, a vital sign estimation based on the extracted signal may be performed by a first vital signs estimation 416. On the other hand, and for the second object 108, the vital sign estimation based on the extracted signal may be performed by a second vital signs estimation 418. The vital signs estimation as described here is further discussed below.

Figure 5:
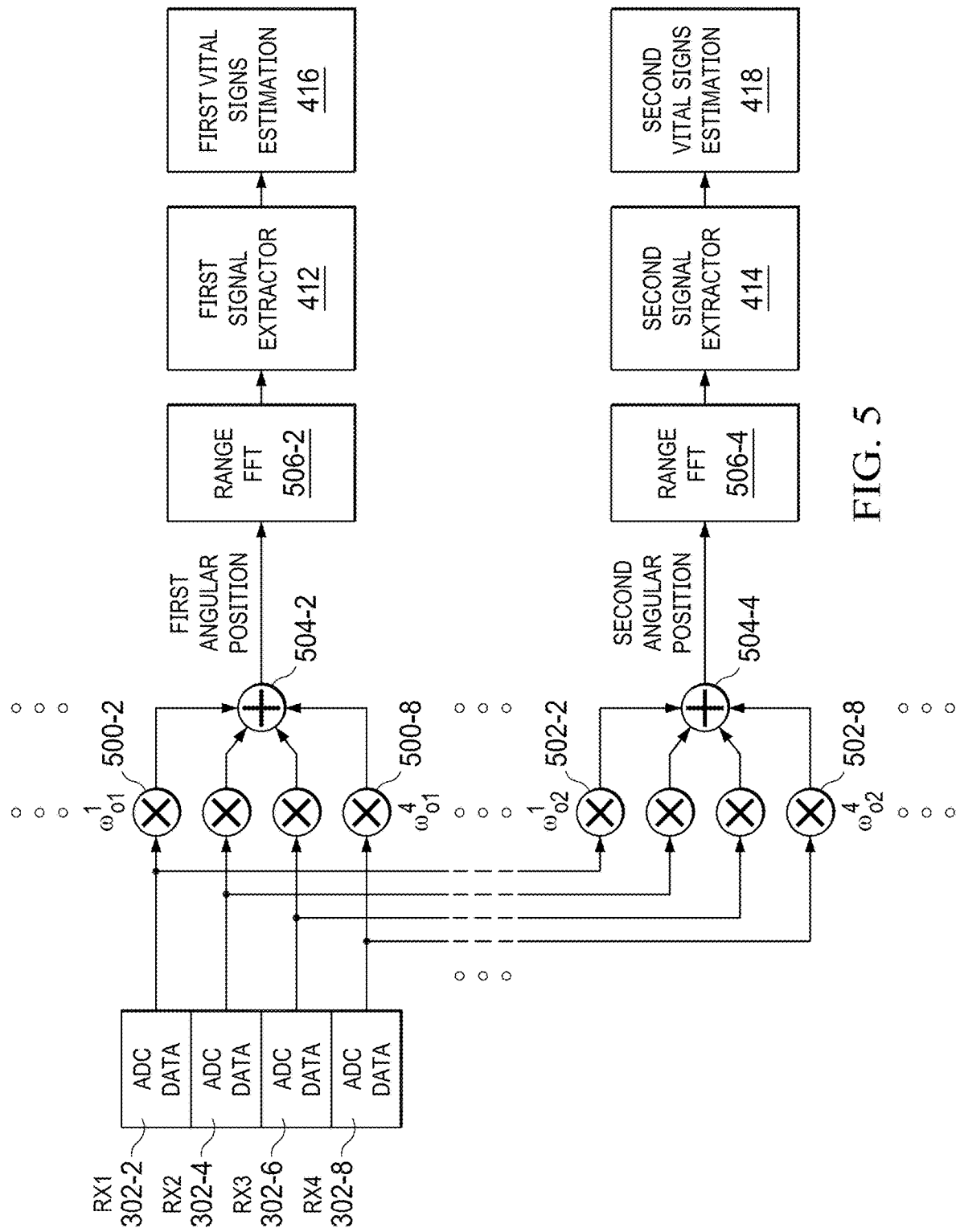
FIG. 5 illustrates an example detection and identification of multiple objects by a mm-wave system as described in present implementations herein.

FIG. 5 describes another embodiment of detection and identification of multiple objects by a mm-wave system. In this implementation, a plurality of transmitters and receivers may allow the use of digital beamforming to mitigate interference from other moving objects and to isolate the objects of interest within the radar field-of-view in a computationally efficient manner. For example, the angles of the first object 106 and the second object 108 may be initially identified through the object detection block 410 as shown in FIG. 4. In this example, and in a case where the angle of the objects are expected to have some changes after a few frames, then the implementation as described in FIG. 4 above may be applied periodically after a certain time period.

In an implementation, once a particular angular positon of the object of interest has been found, beamforming weights may be computed based on the found angular position. In this implementation, the beamforming weights may be calculated through beamforming techniques or methods such as using a classical beamformer method, MVDR, etc.

For example, after the initial identification of the object through the object detection block 410 as shown in FIG. 4, beamforming weights 500-2 . . . 500-8 (beamforming weights 500) for identified object (e.g., first object 106) located on a first angular position may include $\omega_{o1} = [\omega_{o1}^1 \omega_{o1}^2 \ldots \omega_{o1}^N]$ where N is the number of virtual receivers. Similarly, beamforming weights 502-2 . . . 502-8 (beamforming weights 502) for another identified object (e.g., second object 108) located on a second angular position may include $\omega_{o2} = [\omega_{o2}^1 \omega_{o2}^2 \ldots \omega_{o2}^N]$ where N is the number of virtual receivers. In this example, the beamforming weights 500 and 502 are multiplied with the ADC data or samples that may be received from each of the virtual receivers.

Thereafter, the product of the weights and the data from the plurality of receivers may be summed up through adder 504 to generate a single stream of data at each output of the adder 504. The signal stream of data at each output of the adder 504, for example, may include a particular first object 106 or the second object 108 from a particular angle as determined by the beamforming weights.

As described herein, a range FFT operation may be implemented by range FFT blocks 506-2 and 506-4 on the single stream of data output of the adders 504-2 and 504-4, respectively. The implemented range FFT operation, for example, may facilitate identification of range-bin that correspond to an identified object. In this example, the phase values from this range-bin are then tracked over time and the processing steps as described in FIG. 6 below may be used to estimate the breathing and heart-rate.

With the identified range-bin from the output of the range FFT blocks 506-2 and 506-4, the first signal extractor 412 and the second signal extractor 414 may be configured to extract signal phases and to determine signal peaks of the corresponding identified objects. Thereafter, the vital signs estimation of the identified objects may be implemented by the first and second vital signs estimation 416 and 418 as described in FIG. 4 above.

In an implementation, the scheme as described in FIG. 5 above may be implemented in scenarios where the object of interest is at known angles with respect to the mm-wave sensor. For example, the described scheme may be applied when the object is expected to sit on a chair or lay on a bed where the angular position of the chair and bed with respect to the sensor would be known a priori.

Figure 6:
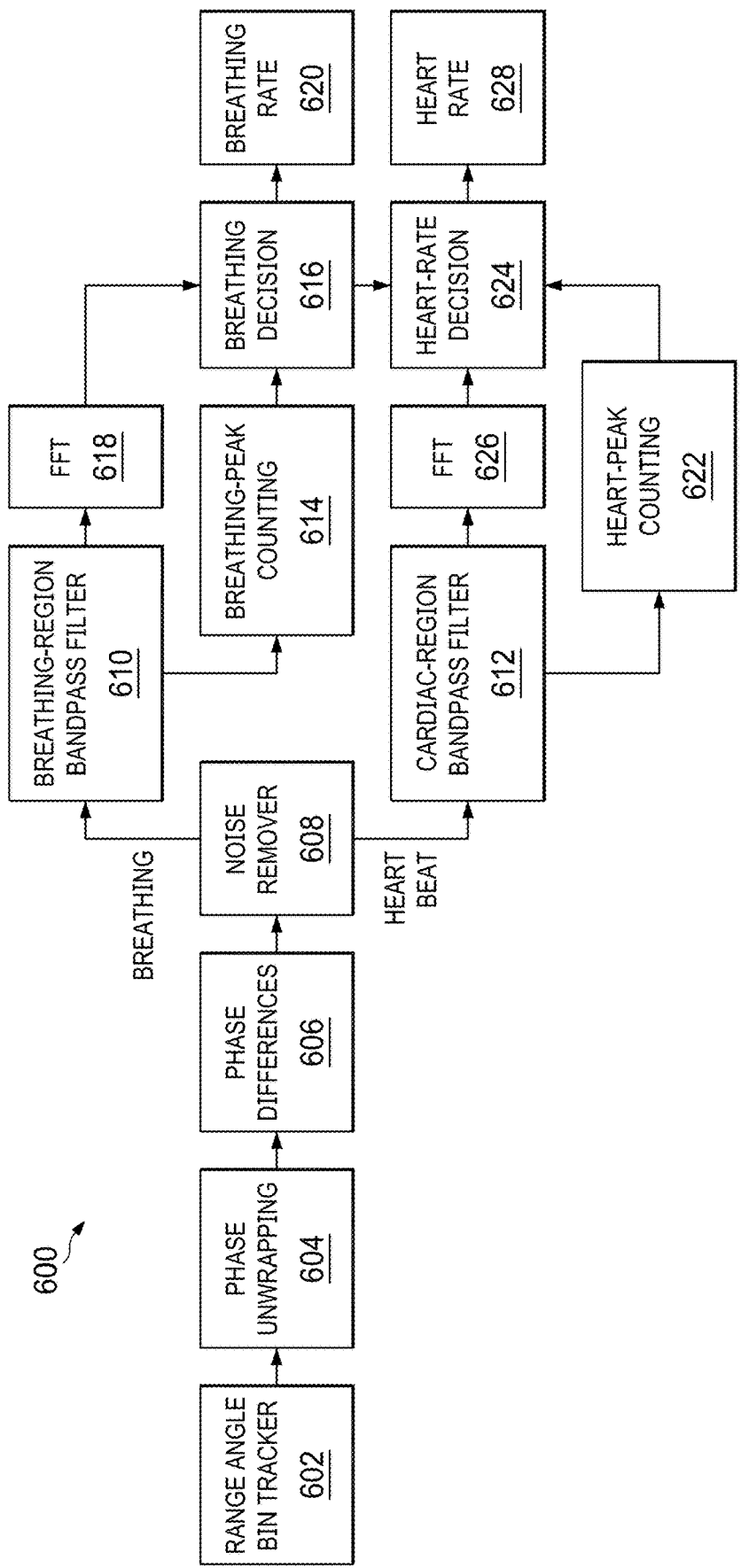
FIG. 6 illustrates an example vital signs estimation by a mm-wave system as described in present implementations herein.

FIG. 6 illustrates an example vital signs estimation 600 by a mm-wave system as described in present implementations herein. The vital signs estimation 600, for example, may implement the first vital signs estimation 416 or the second vital signs estimation 418 as described in FIG. 4 above. In this example, the vital signs estimation 600 may facilitate the detection of breathing and heart rates of the identified object as described in FIG. 4.

In an implementation, a range angle bin tracker 602 may include extracted signals containing the signal phases tracked over time from a range-angle bin on the range-azimuth plane 408. That is, the extracted signals may be extracted through the first signal extractor 412 and the second signal extractor 414 as discussed above.

For example, referencing the determined first object 106 or person identified through the object detection 410, the range angle bin tracker 602 may include the extracted signal for the first vital signs estimation 416 that may represent a waveform signal that contains the body displacement due to heart-beat and breathing of the first object 106 or person. In this example, the extracted signal may be further filtered, processed, and analyzed to determine the exact breathing and heart rates of the object or person.

The processing may include, for example, a phase unwrapping 604 that may be configured to unwrap the extracted signal by adding or subtracting "$2\pi$" in a case where a phase difference that is detected between consecutive phase values of the extracted signal is greater than "$\pi$". In this example, a computation of the phase differences between successive unwrapped phase values to generate phase differences 606 may remove signal drifts in the signal phases and enhance the heart-beat signal.

Thereafter, a noise remover 608 may be implemented to filter noise, remove peaks that are out-of-range from breathing and heart rate thresholds, and the like, of the signals in the generated phase differences 606. For example, an impulse-like noise may be removed by computing a forward a(n)-a(n+1) and backward a(n)-a(n−1) difference for each a(n) where a(n) is the unwrapped differential phase value. In this example, the computed differences may be compared to a threshold and in response to computed differences that exceed the threshold, the a(n) may be replaced by an interpolated value.

After the noise filtering at the noise remover 608, the noise filtered signal may be further bandpass filtered by a breathing-region band pass filter 610 and a cardiac-region bandpass filter 612 to separate out the breathing and cardiac region waveforms, respectively. A person's breathing (i.e., 0.1-0.5 Hz) may be substantially slower as compared to the heart rate (i.e., 0.8-2.0 Hz). In this case, the bandpass filtering by the breathing region bandpass filter 610 and the cardiac region bandpass filter 612 may isolate breathing rate signals and heart rate signals, respectively. Furthermore, bandpass filtering may minimize the impact of spectral leakage of the breathing signal on the heart-beat signal. The cutoff frequencies of these bandpass filters can be adjusted based on the use-cases. For example babies might have a higher breathing and heart rate than adults and the cutoff frequencies may be adjusted accordingly.

In measuring breathing rate, a breathing-peak counting block 614 may be configured to receive breathing signal waveforms from the first bandpass filter 610 and filter signal peaks of the breathing signal waveform in order to generate, for example, an estimated breathing rate based on a number of the filtered signal peaks. In this example, peak filtering is done as follows: two thresholds i.e. Minimum Peak Distance ($P_{min}$) and Maximum Peak Distance ($P_{max}$) are defined based on the sampling rate and allowed breathing-rate frequency range (for an adult this would be 0.1-0.5 Hz). The first peak in the waveform is chosen as a valid peak and the next valid peak is chosen such that the distance between the current peak and the previous valid peak is within the interval [$P_{min}$ to $P_{max}$]. Additionally peak can be rejected based on if their amplitudes are too high or too low based on the expected breathing signal amplitudes. After isolating the valid signal peaks, a breathing rate is estimated based on the average of the inter-peak distances for all the valid peaks. Thereafter, the estimated breathing rate may be forwarded to a breathing decision 616, which further receives another breathing rate estimate from a FFT 618.

The FFT 618, for example, may be configured to receive the breathing signal waveforms from the breathing-region bandpass filter 610, and perform the FFT algorithm on the received breathing signal waveform in order to generate the estimated breathing rate. Pre-processing steps of gain control and windowing may be done prior to the FFT processing. In the gain control step, the energy is computed over a moving window of length L and if this energy is above a threshold, the waveform values for this window are scaled down. This threshold value is chosen based on the known amplitude limits of the breathing waveforms. Similar to the breathing-peak counting 614 above, the output of the FFT 618 may be received by the breathing decision 616 that may be configured to generate a breathing rate 620.

For example, the breathing decision 616 may be configured to estimate the breathing-rate using the maximum value peak in the breathing spectrum obtained from the FFT 618 and computing the confidence metric. The confidence metric may be calculated as the ratio of the signal power in the frequency bins of (and around) the peak over the remaining frequency bins in the breathing spectrum. If the confidence metric exceeds a certain threshold then the FFT-based breathing-rate estimate is chosen as a valid breathing-rate. Otherwise the breathing-rate estimated by the peak counting method 614 is chosen. The valid breathing rate may be stored in a circular buffer and the breathing-rate 620 is computed based on the median value of the valid breathing-rate values within this circular buffer.

In measuring the heart rate, a heart-peak counting 622 may be configured to receive heart rate—signal waveforms from the second bandpass filter 612 and filter signal peaks of the received heart rate—signal waveforms in order to generate, for example, an estimated heart rate based on a number of the filtered signal peaks. In this example peak filtering is done as follows, two thresholds i.e. Minimum Peak Distance ($P_{min}$) and Maximum Peak Distance ($P_{max}$) are defined based on the sampling rate and allowed heart-rate frequency range (for adults this would be 0.8-2.0 Hz). The first peak in the waveform is chosen as a valid peak and the next valid peak is chosen such that the distance between the current peak and the previous valid peak is within the interval [$P_{min}$ to $P_{max}$]. Additionally peak can be rejected based on if their amplitudes are too high or too low based on the expected heart-beat signal amplitudes. After isolating the valid signal peaks, a heart-rate is estimated based on the average of the inter-peak distances for all the valid peaks. Thereafter, the estimated heart rate may be forwarded to a heart-rate decision 624, which further receives another heart rate estimate from a FFT 626 and the breathing decision 616.

The FFT 626, for example, may be configured to receive the heart-beat signal waveforms from the first bandpass filter 612, and perform the FFT algorithm on the received heart-beat signal waveform in order to generate the estimated heart-rate. Pre-processing steps of gain control and windowing may be done prior to the FFT processing. In the gain control step, the energy is computed over a moving window of length L and if this energy is above a threshold, the waveform values for this window are scaled down. This threshold value is chosen based on the known amplitude limits of the heart-beat waveforms.

The heart-rate decision block 624 may be configured to estimate the heart rate 628 using the maximum value peak in the cardiac spectrum obtained from the FFT 626 and computing the associated confidence metric. The maximum value peak in the cardiac spectrum is identified and chosen as the FFT based heart-rate estimate. Furthermore, a confidence metric is also computed for the FFT-based heart-rate estimate. The confidence metric is calculated as the ratio of the signal power in the frequency bins of (and around) the peak over the remaining frequency bins in the cardiac spectrum If the confidence metric exceeds a certain threshold then the FFT-based heart-rate estimate is chosen as a valid heart-rate otherwise the heart-rate estimated by the peak counting method 622 is chosen. The valid heart-rate is stored in a circular buffer and the heart-rate 628 can be computed based on the median value of the valid heart-rate values within this circular buffer.

With the estimated heat rate from the heart-peak counting 622 and the FFT 626, the heart-rate decision 624 may further consider breathing rate output of the breathing decision 616 in order to remove the peaks corresponding to the breathing harmonics in the cardiac spectrum obtained from the FFT 626.

The maximum peak in the cardiac spectrum may not necessarily correspond to the heart-rate. That is, breathing harmonics, noise sources, body movements, and the like may add to larger magnitude peaks than the actual heart rate peak. In this regard, the heart-rate decision block 624 may be configured to perform a density-based heart-rate estimate, where the heart-rate is determined based on the number of occurrences of the spectral peaks within a given time frame as opposed to making an estimate based on the maximum value peak in the cardiac spectrum as discussed in the foregoing paragraph. The density-based heart-rate estimate is performed as: find all peaks in the cardiac spectrum and retain top N peaks where N is an integer number; remove the peaks (from the top N peaks) that correspond to breathing harmonic; place the remaining peaks in the circular buffer; accumulate the peaks for T seconds; use a clustering algorithm such as a db scan algorithm to divide the accumulated peaks into clusters; determine the cluster with the maximum number of peaks; and choose the median peak value of the determined cluster as valid median heart-rate value i.e., heart rate 628.

Figure 7:
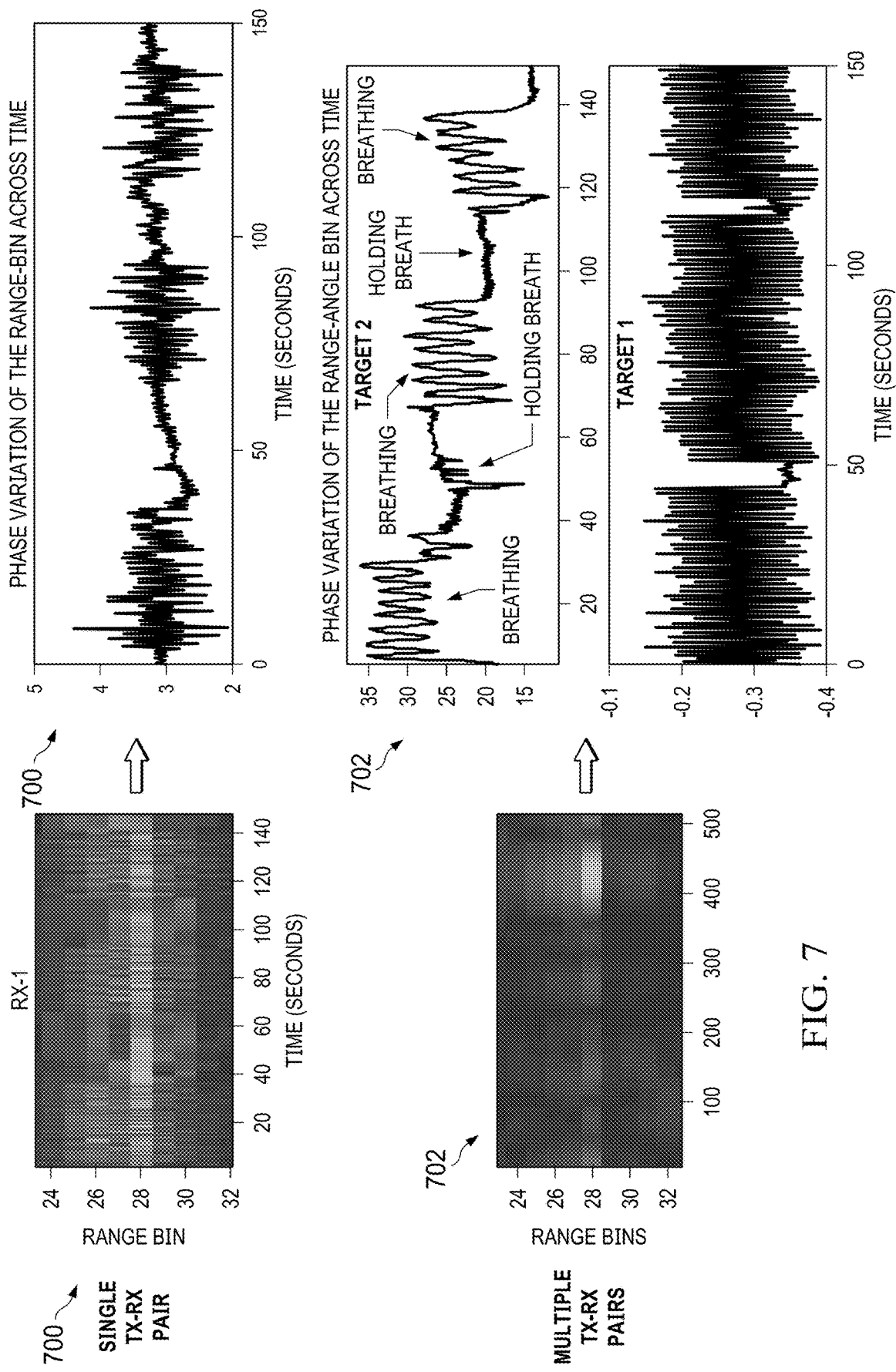
FIG. 7 illustrates an example of extracted signals as described in present implementations herein.

FIG. 7 shows example extracted signals as described in present implementations herein. Referencing FIG. 4 above, the object detection 410 may be configured to use the angle measurements from the range-azimuth plane 408 in identifying and isolating one object (e.g., first object 106) from another object (e.g., second object 108). However, in a case where the reflected signals 114 that may be received by the ADC 400 were derived from a single TX-RX pair (i.e., minimal number of transmitter and receiver were used), the resulting range-azimuth plane 408 may hardly identify or generate signals that may show difference in angles or phases of the reflecting objects.

As shown in FIG. 7, an output signal of the mm-wave system 104 when using a single TX-RX pair (e.g., one TX1 300-2 and one RX1 302-2) may generate a signal 700 with indistinguishable or vague representations of the different signal reflections from multiple objects. As opposed to signal 702 where the use of plurality of receivers (in either MIMO or non-MIMO form) is used by the mm-wave system 104, the breathing rate signal waveforms and the heart rate waveforms from multiple targets or objects may be identified and isolated from one another. In other words, the use of plurality of receive antennas (i.e., large number of virtual antennas) may facilitate generation of the signals that may show clearly the difference in angles or phases to identify each object from the multiple reflecting objects.

Figure 8:
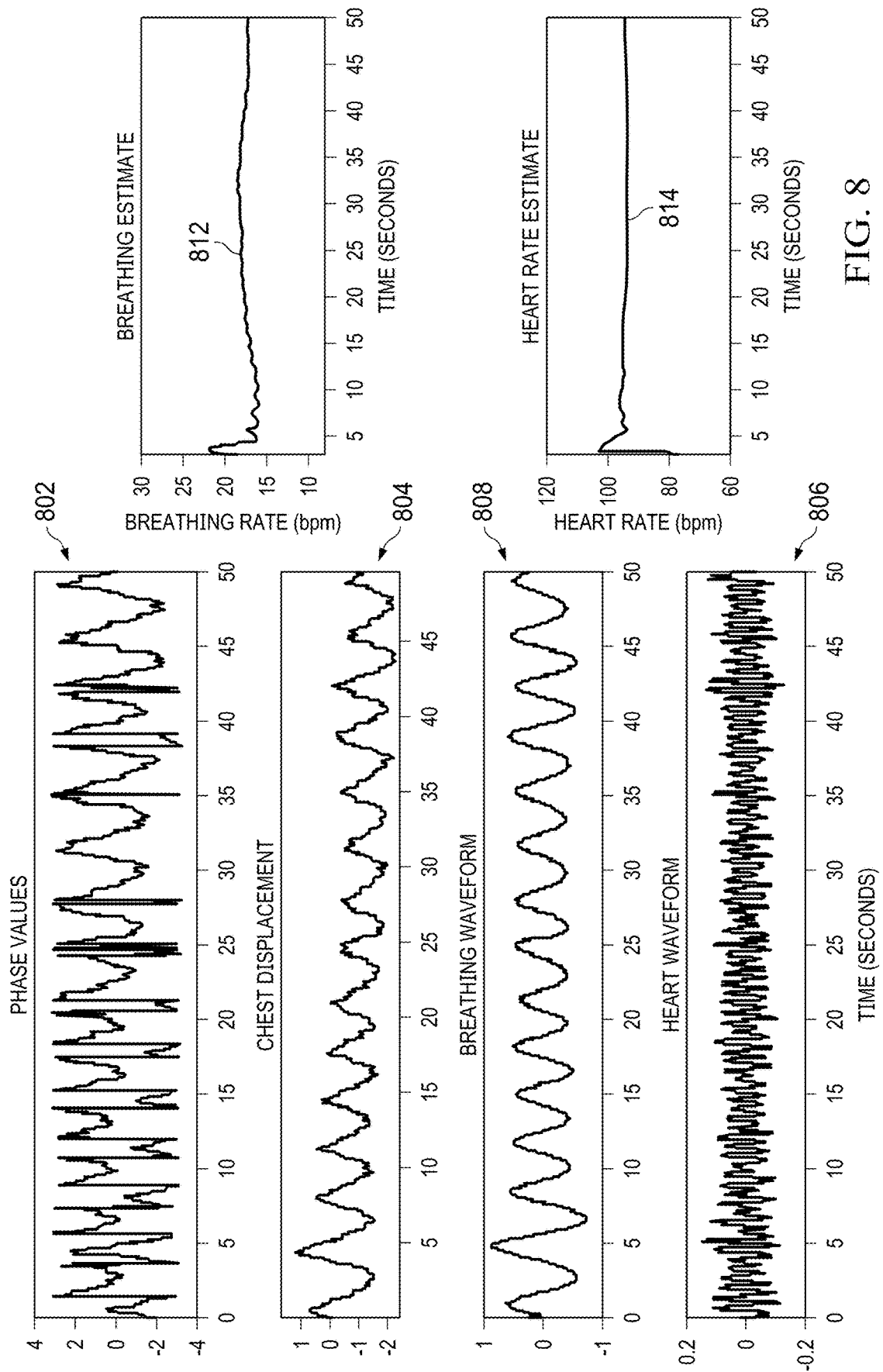
FIG. 8 illustrates example components of an extracted signal that corresponds to an identified object as described herein.

FIG. 8 shows example components of an extracted signal that corresponds to an identified object as described herein. As shown, an extracted signal graph represented by phase variations 802 may correspond to an output of the first signal extractor 412 or the second signal extractor 414. For example, the extracted signal graph-phase variations 802 may include the phase measurements from the first object 106, second object 108, or the third object 110. Based from the extracted phase variations 802, the phase unwrapping 604 may generate a signal that may be represented by chest displacement graph 804.

Based from the generated chest displacement graph 804, additional signal processing of computing the phase differences 606 between adjacent samples and noise remover 608 may be implemented on the chest displacement graph 804 prior to bandpass filtering. The bandpass filtering process by the breathing-region band pass filter 610 and the cardiac-region bandpass filter 612 may generate breathing signal waveform 806 and heart-beat signal waveform 808, respectively. The heart signal waveform 808 and the breathing signal waveform 806 are components of the chest displacement graph 804.

After the determination of the heart signal waveform 808 and the breathing signal waveform 806 components, the breathing decision 616 and the heart-rate decision 624 from FIG. 6 above may thereafter generate breathing estimate graph 812 and heart rate estimate graph 814, respectively.

Figures 9, 10:
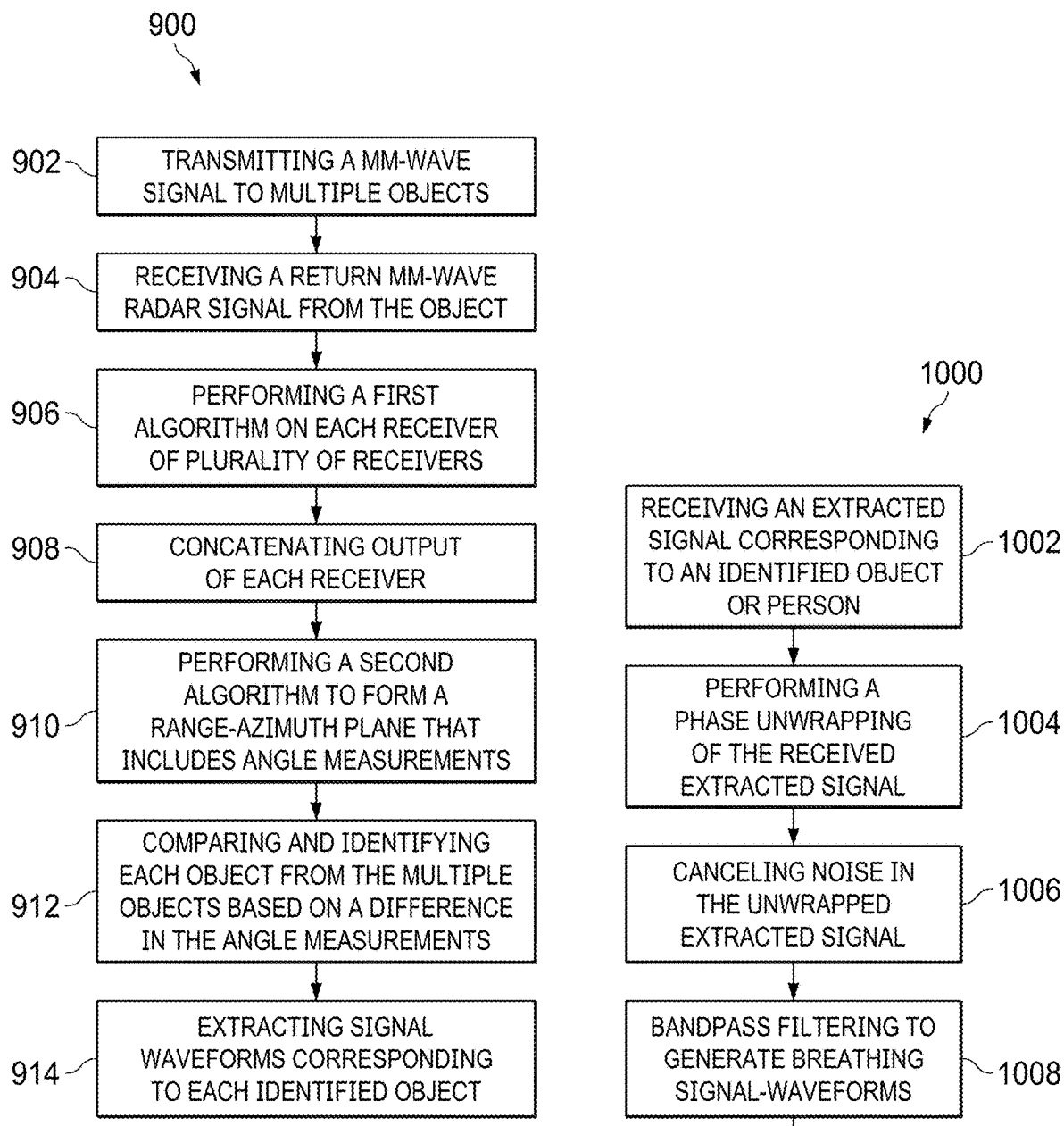
FIG. 9 illustrates an example process chart illustrating an example method for monitoring, detecting, and identifying multiple objects by a mm-wave system as described herein.
FIG. 10 illustrates an example process chart illustrating an example method for determining breathing rate by a mm-wave system as described herein.

FIG. 9 shows an example process chart 900 illustrating an example method for monitoring, detecting, and identifying multiple objects by a mm-wave system as described herein. The order in which the method is described is not intended to be construed as a limitation, and any number of the described method blocks can be combined in any order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

At block 902, transmitting a mm-wave signal by one or a plurality of transmitters to multiple objects is performed. For example, the plurality of transmitters 300 of the mm-wave system 104 transmit mm-wave signals 112 to the direction of the object such as the first object 106 and the second object 108. In this example, the mm-wave signals 112 may include FMCW mm-wave signal.

At block 904, receiving by a plurality of receivers of return-mm-wave signals from the multiple objects is performed. For example, the plurality of receivers 302 may be configured to receive return-mm-wave signals 114 that include signal reflections from the first object 106 and the second object 108.

At block 906, performing a first algorithm on each receiver of the plurality of receivers to form a range-antenna plane is performed. For example, the first receiver 202-2 and the second receiver 202-4 of the plurality of receivers 302 may be configured to perform FFT algorithm in order to transform the time-domain digital reflected mm-wave signals 114 into frequency-domain digital reflected mm-wave signals 114. In this example, the output of the range-FFT 402 may include complex-valued samples (i.e., samples with magnitudes and phases) for each receiver of the plurality of receivers 302. The different signal magnitudes and signal phases on each receiver of the plurality of receivers 302 may be utilized to identify and distinguish one reflecting object from another reflecting object.

At block 908, concatenating output of each receiver of the plurality of receiver is performed. For example, the output of the range-FFT 402 for each receiver i.e., the complex-valued samples of each receiver of the plurality of receivers 302, are concatenated to generate a range-antenna plane 404. In the 2TX by 4RX mm-wave system that may generate a total of eight virtual receivers, the range-antenna plane 404 may include a series of combined complex-valued samples from each of the 8 virtual receivers. The series of combined complex-valued samples may include the signal magnitudes and phases as seen from the eight virtual receivers (i.e., plurality of receivers 302).

At block 910, performing a second algorithm on the concatenated output to form a range-azimuth plane is performed. For example, the direction of arrival 406 may perform another FFT algorithm and taking into consideration an RX-dimension for each range bin from the range-antenna plane 404. In this example, the angle of arrival may be derived from difference in phases in between receivers of the plurality of receivers. In this example still, the output of the direction of arrival 406 may be represented by a formed range-azimuth plane 408.

At block 912, comparing and identifying each object from the multiple objects based on the formed range-azimuth plane is performed. For example, the object detection 410 may be configured to determine the different objects based from the range-azimuth plane 408 by utilizing, for example, the CFAR algorithm or other types of detection schemes to determine the different objects. In this example, the CFAR algorithm may compare angle differences between the subjects.

At block 914, extracting signal corresponding to each identified object is performed. For example, the first-signal extractor 412 and the second—signal extractor 414 may be configured to extract the phase value in the range-azimuth plane 408 based on the range-angle bin identified for each of the multiple objects. These phase values are tracked over time by a user-determined window length which can be from 5 to 30 seconds. In this example, the first signal extractor 412 and the second signal extractor 414 may extract the signals that correspond to the first object and the second object, respectively.

FIG. 10 shows an example process chart 1000 illustrating an example method for determining breathing rate by a mm-wave system as described herein. The order in which the method is described is not intended to be construed as a limitation, and any number of the described method blocks can be combined in any order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

At block 1002, receiving an extracted signal corresponding to an identified object or person is performed. For example, the first-signal extractor 412 and the second-signal extractor 414 may extract the signals that correspond to the first object 106 and the second object 108, respectively. In this example, the receiving of the extracted signal may include the signal corresponding to either the identified first object or the second object.

At block 1004, performing a phase unwrapping of the received extracted signal to generate phase differences is performed. For example, the phase unwrapping 604 may be configured to unwrap the extracted signal by adding or subtracting "2π" in a case where a phase difference that is detected between consecutive phase values of the extracted signal is greater than "π". In this example, the computation of the phase differences between successive unwrapped phase values may generate phase differences 606, which excludes the signal drifts in the signal phases.

At block 1006, cancelling noise from the unwrapped extracted signal is performed. For example, the noise remover 608 may be implemented to filter noise, remove peaks that are out-of-range from breathing and heart rate thresholds, and the like, of the signals on the generated phase differences 606.

At block 1008, bandpass filtering the extracted signal to generate breathing signal waveforms is performed. For example, the bandpass filtering by the breathing region bandpass filter 610 and the cardiac-region bandpass filter 612 may isolate breathing rate signals and heart rate signals, respectively.

At block 1010, performing a peak counting and a FFT algorithm on the breathing signal waveforms is performed. For example, the breathing-peak counting 614 may be configured to receive breathing signal waveforms from the breathing-region bandpass filter 610 and filter signal peaks of the breathing signal waveform in order to generate an estimated breathing rate based on a number of the filtered signal peaks. In this example, peak filtering may be done by defining two thresholds i.e. Minimum Peak Distance ($P_{min}$) and Maximum Peak Distance ($P_{max}$) based on the sampling rate and allowed vital signs frequency range (for Breathing adult this would be 0.1-0.5 Hz). The first peak in the waveform is chosen as a valid peak and the next valid peak is chosen such that the distance between the current peak and the previous valid peak is within the interval [$P_{min}$ to $P_{max}$]. Additionally, peaks can be rejected based on if their amplitudes are too high or too low based on the expected breathing signal amplitudes. After isolating the valid signal peaks a breathing rate is estimated based on the average of the inter-peak distances for all the valid peaks. Thereafter, the estimated breathing rate may be forwarded to a breathing decision 616, which further receives another breathing rate estimate from a FFT 618.

Similarly, the FFT 618, for example, may be configured to receive the breathing signal waveforms from the breathing-region bandpass filter 610, and perform the FFT algorithm on the received breathing signal waveform in order to generate the estimated breathing rate.

At block 1012, determining breathing rate based from the performed peak-counting and FFT algorithm is performed. The breathing decision 616 may receive outputs from the breathing-peak counting 614 and the FFT 618. Based from these outputs, the breathing decision 616 may be configured to generate the breathing rate 620.

Figure 11:
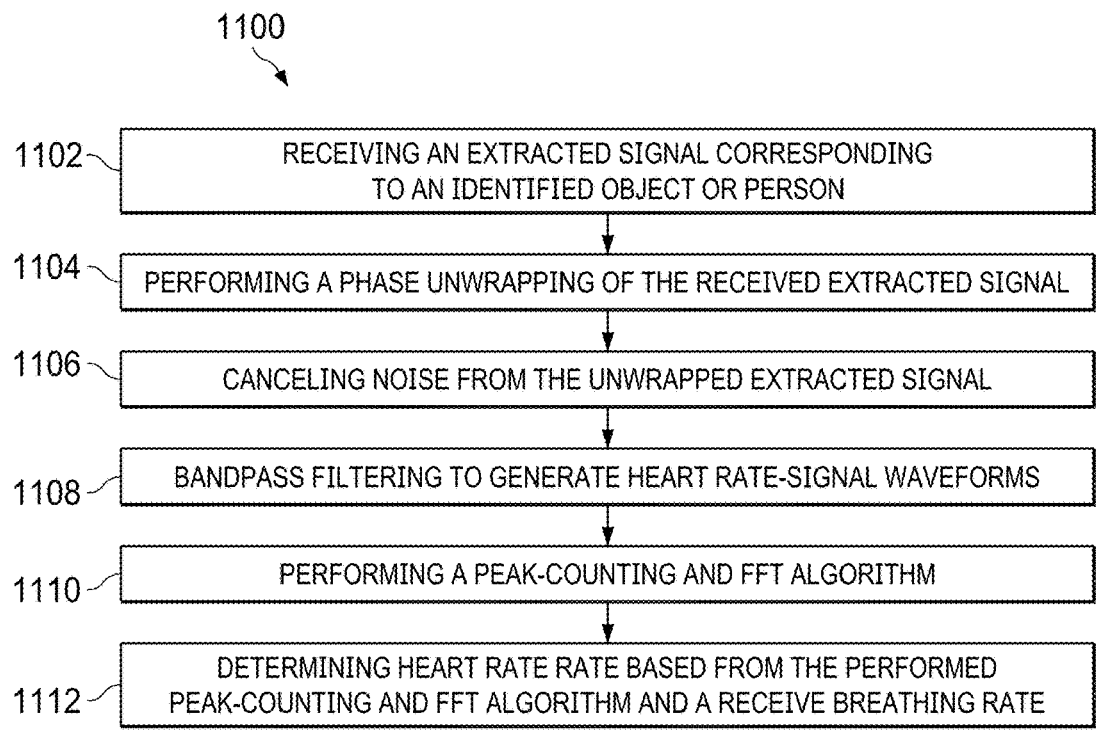
FIG. 11 illustrates an example process chart illustrating an example method for determining heart rate by a mm-wave system as described herein.

FIG. 11 shows an example process chart 1100 illustrating an example method for determining heart rate by a mm-wave system as described herein. The order in which the method is described is not intended to be construed as a limitation, and any number of the described method blocks can be combined in any order to implement the method, or alternate method. Additionally, individual blocks may be deleted from the method without departing from the spirit and scope of the subject matter described herein. Furthermore, the method may be implemented in any suitable hardware, software, firmware, or a combination thereof, without departing from the scope of the invention.

Blocks 1102-1106 and 1110 may adopt the same procedures as described on Blocks 1002-1006 and 1010, respectively. The difference, however, is at block 1108 where the bandpass filtering generates the heart rate—signal waveforms rather than the breathing rate signal waveforms. Furthermore, at block 1112, the determining of the heart rate is based upon the FFT algorithm output and the performed peak-counting output of the FFT 526 and heart-peak counting 522, respectively. In addition, the determining of the heart rate is further based on the breathing rate as determined in block 1012 of FIG. 10. That is, the heart-rate decision 524 further receives the output of the breathing decision 516 in estimating the heart rate 528.

What is claimed is:

1. A method of monitoring one or more subjects comprising:
    transmitting, by a first transmitter, a frequency-modulated continuous wave millimeter wave (mm-wave) signal at a wavelength to the one or more subjects;
    receiving, through multiple receivers, a first set of return mm-wave signals from the one or more subjects in response to transmitting the frequency-modulated continuous wave mm-wave signal;
    re-transmitting, by a second transmitter, the frequency-modulated continuous wave mm-wave signal at the wavelength to the one or more subjects, wherein the first transmitter and the second transmitter are separated by a first distance of two times the wavelength;
receiving, through the multiple receivers, a second set of return mm-wave signals from the one or more subjects in response to re-transmitting the frequency-modulated continuous wave mm-wave signal, wherein the multiple receivers are each separated by a second distance of one-half of the wavelength, wherein the first transmitter and each of the multiple receivers form a first set of virtual receivers and the second transmitter and each of the multiple receivers form a second set of virtual receivers, and wherein the first set of virtual receivers and the second set of virtual receivers form a virtual linear array of receivers;
performing a first Fast Fourier Transform (FFT) algorithm on the first and second set of return mm-wave signals of each virtual receiver of the virtual linear array of receivers to generate a plurality of virtual receiver outputs;
concatenating the plurality of virtual receiver outputs from each virtual receiver of the virtual linear array of receivers to generate a range-antenna plane, wherein the range-antenna plane comprises signal magnitudes and phases as seen from the virtual linear array of receivers;
performing a second FFT algorithm on the range-antenna plane to determine angle measurements of each subject to generate a range-azimuth plane;
comparing and identifying different subjects based upon a difference in the angle measurements between the different subjects; and
extracting, over a period of time, a plurality of phase values in the range-azimuth plane that are each based on a range-angle bin associated with each of the different subjects, wherein the period of time is 5 to 30 seconds.

2. The method of claim 1 further comprising:
retransmitting through a second transmitting channel the mm-wave signal to the one or more subjects;
receiving through the virtual linear array of receivers, different return mm-wave signals from the one or more subjects; and
combining the different received mm-wave signals for each of the one or more subjects.

3. The method of claim 1, wherein the return mm-wave signals are reflected versions of the transmitted millimeter wave signal.

4. The method of claim 1, wherein the concatenated virtual receiver outputs include signal magnitudes and peaks of each virtual receiver of the virtual linear array of receivers.

5. The method of claim 1, wherein the second FFT algorithm is performed on each range-bin of the generated range-antenna plane to derive phase differences in between each virtual receiver of the virtual linear array of receivers.

6. The method of claim 1 further comprising:
measuring vital signs of the identified subject, the measuring comprises:
extracting signal waveforms that correspond to the identified subject;
performing a phase unwrapping of the extracted signal waveforms;
determining phase differences of the phase unwrapped extracted signal waveforms;
cancelling noise in the phase unwrapped extracted signal waveforms;
bandpass filtering the signal waveforms to determine a breathing waveform;
performing a peak-counting on the breathing waveform;
applying a window and gain control on the breathing waveform and performing the FFT algorithm; and
determining a breathing rate based on the performed peak-counting and the FFT algorithm.

7. The method of claim 1 further comprising:
measuring vital signs of the identified subject, the measuring comprises:
extracting signal waveforms that correspond to the identified subject;
performing a phase unwrapping of the extracted signal waveforms;
determining phase differences of the phase unwrapped signal waveforms;
cancelling noise in the phase unwrapped extracted signal waveforms;
bandpass filtering the signal waveforms to determine a heart-rate waveform;
performing a peak-counting on the heart-rate waveform;
applying a window and gain control on a heart-beat waveform and performing the FFT algorithm; and
determining a heart-rate based on the performed peak-counting and the FFT algorithm.

8. The method of claim 7, wherein the determining of the heart-rate is further based upon a derived breathing rate of the identified person.

9. A millimeter wave (mm-wave) system comprising:
a plurality of transmitters configured to each transmit a frequency-modulated continuous wave millimeter wave (mm-wave) signal at a wavelength to one or more subjects, wherein each of the plurality of transmitters is separated by a first distance of two times the wavelength;
a plurality of receivers configured to receive return mm-wave signals from the one or more subjects from each of the plurality of transmitters, wherein each of the plurality of transmitters and the plurality of receivers form respective sets of virtual receivers, wherein the respective sets of virtual receivers form a virtual linear array of receivers, and wherein each of the plurality of receivers is separated by a second distance of one-half of the wavelength;
a processor coupled to the plurality of transmitters and receivers, the processor is configured to:
perform a first Fast Fourier Transform (FFT) algorithm on the received return mm-wave signals of each virtual receiver of the virtual linear array of receivers to generate a plurality of virtual receiver outputs;
concatenate the plurality of virtual receiver outputs from each virtual receiver of the virtual linear array of receivers to generate a range-antenna plane, wherein the range-antenna plane comprises signal magnitudes and phases as seen from the virtual linear array of receivers;
perform a second FFT algorithm on the range-antenna plane to determine angle measurements of each subject to generate a range-azimuth plane;
compare and identify different subjects based upon a difference in the angle measurements between the different subjects; and
extract, over a period of time, a plurality of phase values in the range-azimuth plane that are each based on a range-angle bin associated with each of the different subjects, wherein the period of time is 5 to 30 seconds.

10. The mm-wave system of claim 9, wherein the return mm-wave signals are reflected versions of the transmitted millimeter wave signal.

11. The mm-wave system of claim 9, wherein the concatenated virtual receiver outputs include signal magnitudes and peaks of each virtual receiver on the virtual linear array of receivers.

12. The mm-wave system of claim 9, wherein the second FFT algorithm is performed on each range-bin of the generated range-antenna plane to derive phase differences in between each virtual receiver of the virtual linear array of receivers.

13. The mm-wave system of claim 9, wherein the processor is further configured to measure vital signs of the identified subject, the measuring comprises:
  extracting signal waveforms that correspond to the identified subject;
  performing a phase unwrapping of the extracted signal waveforms;
  determining phase differences of the phase unwrapped signal waveforms;
  cancelling noise in the unwrapped extracted signal waveforms;
  bandpass filtering the signal waveforms to determine a breathing waveform;
  performing a peak-counting on the breathing waveform;
  applying a window and gain control on the breathing waveform and performing the FFT algorithm; and
  determining a breathing rate based on the performed peak-counting and the FFT algorithm.

14. The mm-wave system of claim 9, wherein the processor is further configured to measure vital signs of the identified subject, the measuring comprises:
  extracting signal waveforms that correspond to the identified subject;
  performing a phase unwrapping of the extracted signal waveforms;
  determining phase differences of the phase unwrapped signal waveforms;
  cancelling noise in the unwrapped extracted signal waveforms;
  bandpass filtering the signal waveforms to determine a heart-rate waveform;
  performing a peak-counting on the heart-rate waveform;
  applying a window and gain control on the heart-rate waveform and performing the FFT algorithm; and
  determining a heart-rate based on the performed peak-counting and the FFT algorithm.

15. The mm-wave system of claim 14, wherein the determining of the heart-rate is further based upon a derived breathing rate of the identified person.

16. A device comprising:
  a processor:
  a system-on-chip (SOC) coupled to the processor, the SOC is configured to:
    transmit, by a first transmitter, a frequency-modulated continuous wave millimeter wave (mm-wave) signal at a wavelength to one or more subjects;
    receive, by a plurality of receivers, a first set of return mm-wave signals from the one or more subjects;
    re-transmit, by a second transmitter, the frequency-modulated continuous wave mm-wave signal at the wavelength to the one or more subjects, wherein the first transmitter and the second transmitter are separated by a first distance of two times the wavelength;
    receive, by the plurality of receivers, a second set of return mm-wave signals from the one or more subjects, wherein the plurality of receivers are each separated by a second distance of one-half of the wavelength, wherein the first transmitter and each of the plurality of receivers form a first set of virtual receivers and the second transmitter and each of the plurality of receivers form a second set of virtual receivers, and wherein the first set of virtual receivers and the second set of virtual receivers form a virtual linear array of receivers
    perform a first Fast Fourier Transform (FFT) algorithm on the received return mm-wave signals for each virtual receiver of the virtual linear array of receivers to generate a plurality of virtual receiver outputs;
    concatenate the plurality of virtual receiver outputs from each virtual receiver of the virtual linear array of receivers to generate a range-antenna plane, wherein the range-antenna plane comprises signal magnitudes and phases as seen from the virtual linear array of receivers;
    perform a second FFT algorithm on the range-antenna plane to determine angle measurements of each subject to generate a range-azimuth plane;
    compare and identify different subjects based upon a difference in the angle measurements between the different subjects; and
    extract, over a period of time, a plurality of phase values in the range-azimuth plane that are each based on a range-angle bin associated with each of the different subjects, wherein the period of time is 5 to 30 seconds.

17. The device of claim 16, wherein the second FFT algorithm is performed on each range-bin of the generated range-antenna plane to derive phase differences in between each virtual receiver of the virtual linear array of receivers.

18. The device of claim 16, wherein the SOC is further configured to measure vital signs of the identified subject, the measuring comprises:
  extracting signal waveforms that correspond to the identified subject;
  performing a phase unwrapping of the extracted signal waveforms;
  determining phase differences of the phase unwrapped signal waveforms;
  cancelling noise in the unwrapped extracted signal waveforms;
  bandpass filtering the signal waveforms to determine a breathing waveform;
  performing a peak-counting on the breathing waveform;
  applying a window and gain control on the breathing waveform and performing the FFT algorithm; and
  determining a breathing rate based on the performed peak-counting and the FFT algorithm.

19. The device of claim 16, wherein the return mm-wave signals are reflected versions of the transmitted millimeter wave signal.

20. The device of claim 16, wherein the SOC is further configured to measure vital signs of the identified subject, the measuring comprises:
  extracting signal waveforms that correspond to the identified subject;
  performing a phase unwrapping of the extracted signal waveforms;
  determining phase differences of the phase unwrapped signal waveforms;
  cancelling noise in the unwrapped extracted signal waveforms;

bandpass filtering the signal waveforms to determine a heart-rate waveform;
performing a peak-counting on the heart-rate waveform;
applying a window and gain control on the heart-rate waveform and performing the FFT algorithm; and
determining a heart-rate based on the performed peak-counting and the FFT algorithm.

* * * * *